US011844633B2

(12) United States Patent
Li et al.

(10) Patent No.: US 11,844,633 B2
(45) Date of Patent: Dec. 19, 2023

(54) FEATURE IDENTIFYING METHOD AND ELECTRONIC DEVICE

(71) Applicants: Acer Incorporated, New Taipei (TW); National Yang-Ming University, Taipei (TW)

(72) Inventors: Chun-Hsien Li, New Taipei (TW); Tsung-Hsien Tsai, New Taipei (TW); Liang-Kung Chen, Taipei (TW); Chen-Huan Chen, Taipei (TW); Hao-Min Cheng, Taipei (TW)

(73) Assignees: Acer Incorporated, New Taipei (TW); National Yang-Ming University, Taipei (TW)

( * ) Notice: Subject to any disclaimer, the term of this patent is extended or adjusted under 35 U.S.C. 154(b) by 972 days.

(21) Appl. No.: 16/703,792

(22) Filed: Dec. 4, 2019

(65) Prior Publication Data
US 2021/0113158 A1 Apr. 22, 2021

(30) Foreign Application Priority Data
Oct. 17, 2019 (TW) ................................ 108137534

(51) Int. Cl.
| | | |
|---|---|---|
| *A61B 5/00* | (2006.01) | |
| *G16H 50/20* | (2018.01) | |
| *G06N 5/04* | (2023.01) | |
| *G06N 20/00* | (2019.01) | |
| *A61B 5/021* | (2006.01) | |
| *G16H 50/30* | (2018.01) | |

(52) U.S. Cl.
CPC .......... *A61B 5/7275* (2013.01); *A61B 5/7246* (2013.01); *A61B 5/7267* (2013.01); *G06N 5/04* (2013.01); *G06N 20/00* (2019.01); *G16H 50/20* (2018.01); *G16H 50/30* (2018.01); *A61B 5/021* (2013.01)

(58) Field of Classification Search
CPC ........ G16H 50/30; G16H 50/20; G16H 50/50; G16H 50/70; A61B 5/7275
See application file for complete search history.

(56) References Cited

U.S. PATENT DOCUMENTS

| | | | | |
|---|---|---|---|---|
| 2004/0230105 A1* | 11/2004 | Geva | ................... | A61B 5/7275 600/509 |
| 2016/0283686 A1* | 9/2016 | Hu | ........................... | G06N 7/01 |
| 2017/0337345 A1 | 11/2017 | Pauws et al. | | |

FOREIGN PATENT DOCUMENTS

| | | |
|---|---|---|
| CN | 101794354 | 8/2010 |
| CN | 103705225 | 4/2014 |
| TW | 201033910 | 9/2010 |
| TW | M552639 | 12/2017 |
| TW | 201801037 | 1/2018 |

OTHER PUBLICATIONS

Chowdhury, Anuva, et al. "Sensor applications and physiological features in drivers' drowsiness detection: A review." IEEE sensors Journal 18.8 (2018): 3055-3067 (Year: 2018).*
Hall, Mark "Correlation-based feature selection for machine learning". Diss. The University of Waikato, 1999. (Year: 1999).*
Jian, D. et al."Feature selection and classification systems for chronic disease prediction: A review", Egyptian Informatics Journal, vol. 19, Issue 3, 2018, pp. 179-189. (Year: 2018).*
Wosiak, A. et al.; Integrating Correlation-Based Feature Selection and Clustering for Improved Cardiovascular Disease Diagnosis, Complexity, vol. 2018, Article ID 2520706, 11 pages, 2018. (Year: 2018).*

\* cited by examiner

*Primary Examiner* — G. Steven Vanni
(74) *Attorney, Agent, or Firm* — JCIPRNET

(57) ABSTRACT

A feature identifying method and an electronic device are provided. The method includes: obtaining a plurality of physiological information obtained by measuring a subject at a plurality of time points in one day; converting the plurality of physiological information into a plurality of correlation features respectively; establishing a plurality of first risk prediction models according to the plurality of correlation features, and identifying at least one first correlation feature from the plurality of correlation features according to the plurality of first risk prediction models; establishing a plurality of second risk prediction models according to the at least one first correlation feature, and identifying, according to the plurality of second risk prediction models, at least one second correlation feature capable of predicting a specific disease from the at least one first correlation feature; and outputting the at least one second correlation feature.

12 Claims, 6 Drawing Sheets

FEATURE IDENTIFYING METHOD AND ELECTRONIC DEVICE

CROSS-REFERENCE TO RELATED APPLICATION

This application claims the priority benefit of Taiwan application no. 108137534, filed on Oct. 17, 2019. The entirety of the above-mentioned patent application is hereby incorporated by reference herein and made a part of this specification.

TECHNICAL FIELD

The invention relates to a feature identifying method and an electronic device.

BACKGROUND

In general, risk prediction equations including the Framingham risk score are currently used in the medical community to predict a risk of cardiovascular disease. However, the methods using these risk prediction equations usually use only systolic pressure and diastolic pressure obtained by performing one single measurement on the subject without considering a determination that integrate multiple systolic pressure and multiple diastolic pressures obtained by performing multiple measurements at multiple different time points in one day.

Therefore, how to use a plurality of blood pressure information of a subject within 24 hours to help the doctors in determining the risk of the subject having or dying from cardiovascular disease is one of the problems to be solved by those skilled in the art. In addition, other than considering the blood pressure information, physiological and blood information may also be taken into consideration to help diagnose the risk. Accordingly, if a feature capable of predicting a specific disease may be obtained from multiple blood information of the subject within 24 hours, the feature can help in determining the risk, and help doctors to accurately and effectively determine the risk of cardiovascular disease.

SUMMARY

The feature identifying method and the electronic device provided by the invention can find features capable of predicting the specific disease from the physiological information (e.g., the blood pressure information) obtained by measuring the subject at the different time points in one day (24 hours).

The invention proposes a feature identifying method for an electronic device, and the method includes: obtaining a plurality of physiological information obtained by measuring a subject at a plurality of time points in one day; converting the plurality of physiological information into a plurality of correlation features corresponding to the plurality of physiological information respectively; establishing a plurality of first risk prediction models according to the plurality of correlation features, and identifying at least one first correlation feature from the plurality of correlation features according to the plurality of first risk prediction models; establishing a plurality of second risk prediction models according to the at least one first correlation feature, and identifying, according to the plurality of second risk prediction models, at least one second correlation feature capable of predicting a specific disease from the at least one first correlation feature; and outputting the at least one second correlation feature.

The invention proposes an electronic device, which includes a processor configured to perform following operations of: obtaining a plurality of physiological information obtained by measuring a subject at a plurality of time points in one day; converting the plurality of physiological information into a plurality of correlation features corresponding to the plurality of physiological information respectively; establishing a plurality of first risk prediction models according to the plurality of correlation features, and identifying at least one first correlation feature from the plurality of correlation features according to the plurality of first risk prediction models; establishing a plurality of second risk prediction models according to the at least one first correlation feature, and identifying, according to the plurality of second risk prediction models, at least one second correlation feature capable of predicting a specific disease from the at least one first correlation feature; and outputting the at least one second correlation feature.

Based on the above, in the feature identifying method and the electronic device of the invention, according to the physiological information obtained by measuring the subject at the different time points in one day (24 hours), the features capable of predicting the specific disease may be found from the physiological information. These features may be used to assist doctors in determining the risk of the specific disease, or used in subsequent model training or medical research.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
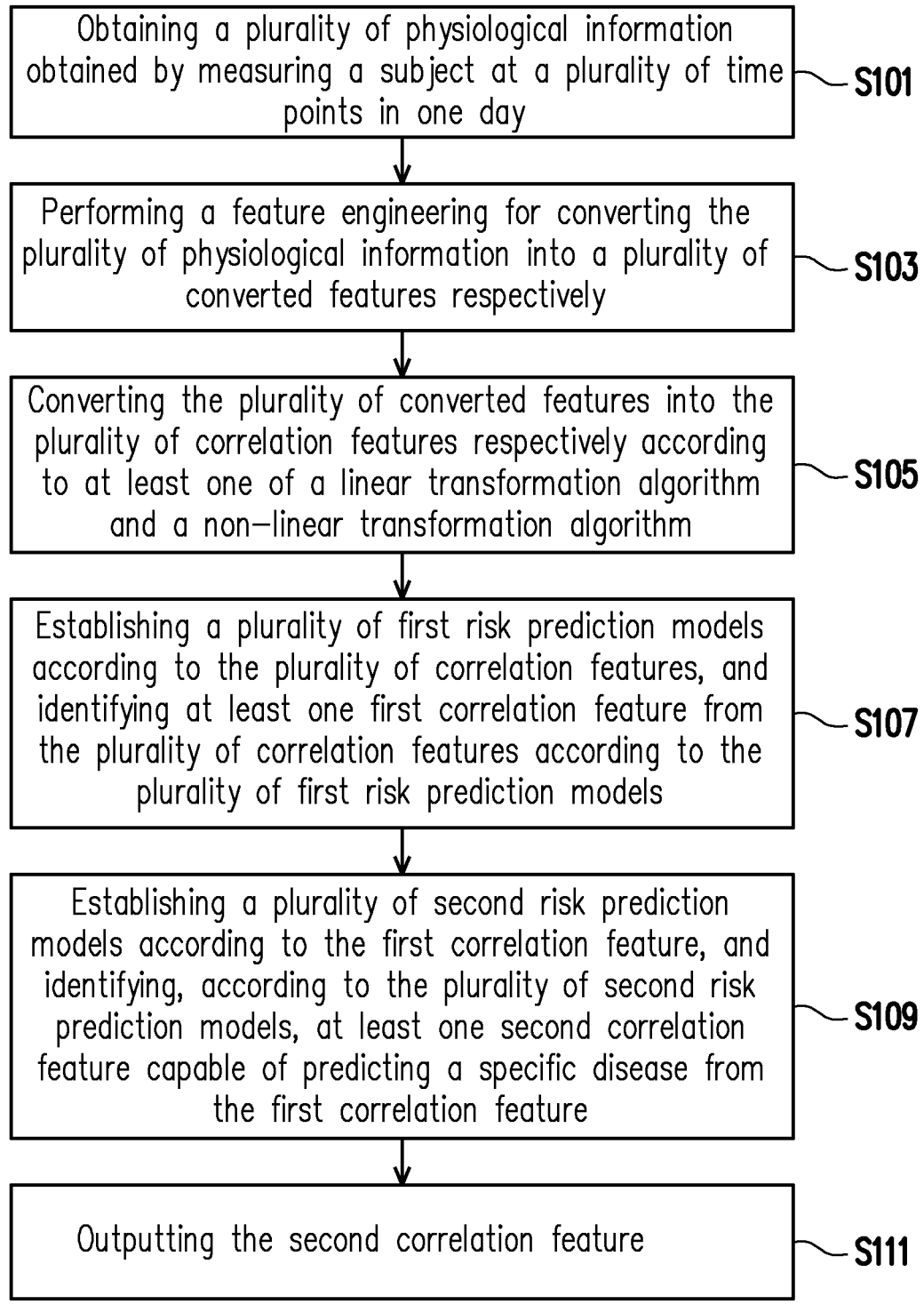
FIG. 1 is a flowchart illustrating a feature identifying method according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

A feature identifying method proposed by the invention is suitable for an electronic device. The electronic device includes a processor, an input/output circuit and a storage circuit. Here, the input/output circuit and the storage circuit are coupled to the processor. The electronic device is, for example, an electronic portable device such as a desktop computer, a server, a cell phone, a tablet computer, a notebook computer and the like, but not limited thereto.

The processor may be a central processing unit (CPU) or other programmable devices for general purpose or special purpose such as a microprocessor and a digital signal processor (DSP), a programmable controller, an application specific integrated circuit (ASIC) or other similar elements or a combination of above-mentioned elements.

The input/output circuit is, for example, an input interface or circuit for obtaining related data from outside the electronic device or from other sources. In addition, the input/output circuit may also transmit data generated by the electronic device to an output interface or circuit of the other electronic device, but not limited thereto.

The memory circuit may be a fixed or a movable element in any possible forms including a random access memory (RAM), a read-only memory (ROM), a flash memory or other similar elements, or a combination of the above-mentioned elements.

In this exemplary embodiment, the storage circuit of the electronic device is stored with a plurality of program code segments. The code segments may be executed by the processor after being installed. For example, the memory circuit is stored with a plurality of modules. Various operations of the electronic device may be executed by those modules, where each of the modules is composed of one or more of the program code segments. However, the invention is not limited in this regard. Each operation of the electronic device may also be implemented in other hardware manners.

FIG. 1 is a flowchart illustrating a feature identifying method according to an embodiment of the invention.

Referring to FIG. 1, in step S101, the processor obtains a plurality of physiological information obtained by measuring a subject at a plurality of time points in one day. In this embodiment, the physiological information is, for example, a blood pressure of the subject, but the invention is not limited thereto. In other embodiments, the physiological information may also be other kinds of physiological information. The following examples are described by using the blood pressure.

In step S103, the processor performs a feature engineering for converting the plurality of physiological information into a plurality of converted features respectively. More specifically, after blood pressure data of the subject is obtained, the feature engineering may be performed to obtain statistics of the blood pressure data (i.e., the converted features described above). The statistics may include an average number, a slope or an oscillation amplitude of the blood pressure data, but not limited thereto.

Then, in step S105, the processor converts the plurality of converted features into the plurality of correlation features respectively according to at least one of a linear transformation algorithm and a non-linear transformation algorithm. Here, the linear transformation algorithm is used to, for example, calculate an average systolic pressure of multiple systolic pressures of each subject measured in one day, and normalize the average systolic pressures of the subjects. More specifically, referring to Table 1:

TABLE 1

|  | Average systolic pressure | Normalized average systolic pressure | Log of average systolic pressure | Square of average systolic pressure | Square root of average systolic pressure | Square of normalized average systolic pressure |
|---|---|---|---|---|---|---|
| Subject U1 | 120 | −0.058 | 4.787 | 14400 | 10.954 | 0.003 |
| Subject U2 | 125 | 0.669 | 4.828 | 15625 | 11.180 | 0.447 |
| Subject U3 | 119 | −0.204 | 4.779 | 14161 | 10.909 | 0.041 |
| Subject U4 | 128 | 1.105 | 4.852 | 16384 | 11.318 | 1.221 |

TABLE 1-continued

|  | Average systolic pressure | Normalized average systolic pressure | Log of average systolic pressure | Square of average systolic pressure | Square root of average systolic pressure | Square of normalized average systolic pressure |
|---|---|---|---|---|---|---|
| Subject U5 | 110 | −1.512 | 4.700 | 12100 | 10.488 | 2.287 |

Taking Table 1 as an example, it is assumed that there are currently subjects U1 to U5. As can be seen in the second column of Table 1, the average systolic pressures of the subjects U1 to U5 in one day are 120, 125, 119, 128, and 110, respectively. In a linear transformation method, the processor may first calculate overall average systolic pressures with a value of 120.4 for the subjects U1 to U5. In addition, the processor may also calculate a standard deviation of the subjects U1 to U5 with a value of 6.8775. Taking the subject U1 as an example, a normalized value (i.e., the normalized average systolic pressure) is $$\frac{(120 - 120.4)}{6.8775} = -0.058.$$

The normalized average systolic pressures of the rest of the subjects U2 to U5 may also be obtained through the above method, which is not repeated hereinafter. The average systolic pressure of each subject is shown in the third column of Table 1.

In addition, the non-linear transformation algorithm is used to, for example, obtain log of the average systolic pressure (the result is shown in the fourth column of Table 1), square of the average systolic pressure (the result is shown in the fifth column of Table 1), or square root of the average systolic pressure (the result is shown in the sixth column of Table 1).

In particular, in step S105, the processor may also convert the plurality of converted features into the plurality of correlation features respectively according to both the linear transformation algorithm and the non-linear transformation algorithm. For example, the linear transformation algorithm may first be used to obtain the normalized average systolic pressure for each subject, and then the non-linear transformation algorithm may be used to obtain square of the normalized average systolic pressure for each subject (the result is shown in the seventh column of Table 1). However, the invention is not intended to limit the actual calculation method when the linear transformation algorithm is used, or when the non-linear transformation algorithm is used, or when the foregoing two are used together.

After the plurality of correlation features are obtained, in step S107, the processor establishes a plurality of first risk prediction models according to the plurality of correlation features, and identifies at least one first correlation feature from the plurality of correlation features according to the plurality of first risk prediction models.

Figure 2A:
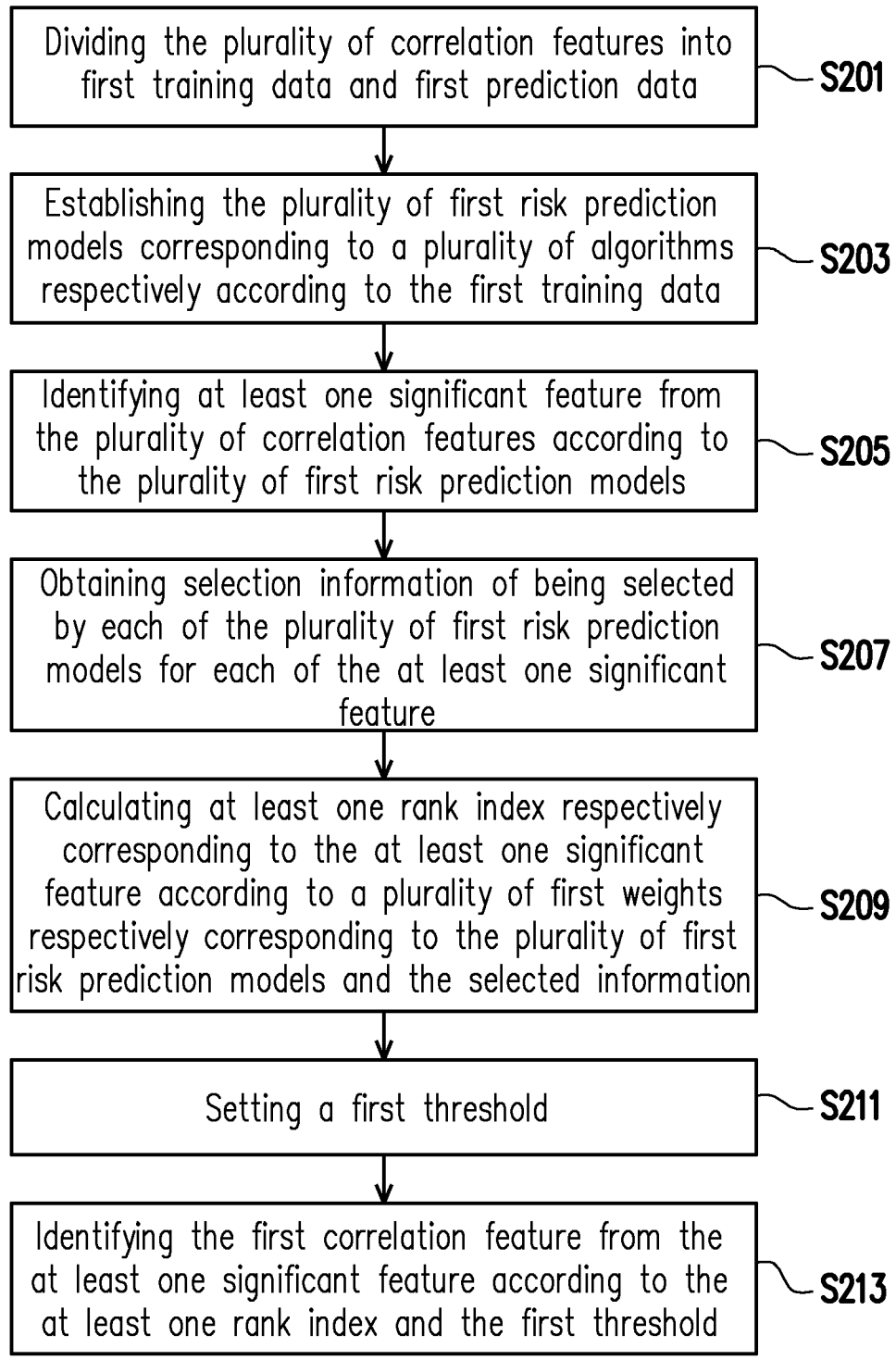
FIG. 2A and FIG. 2B are detailed flowcharts illustrating step S107 according to an embodiment of the invention.
Figure 2B:
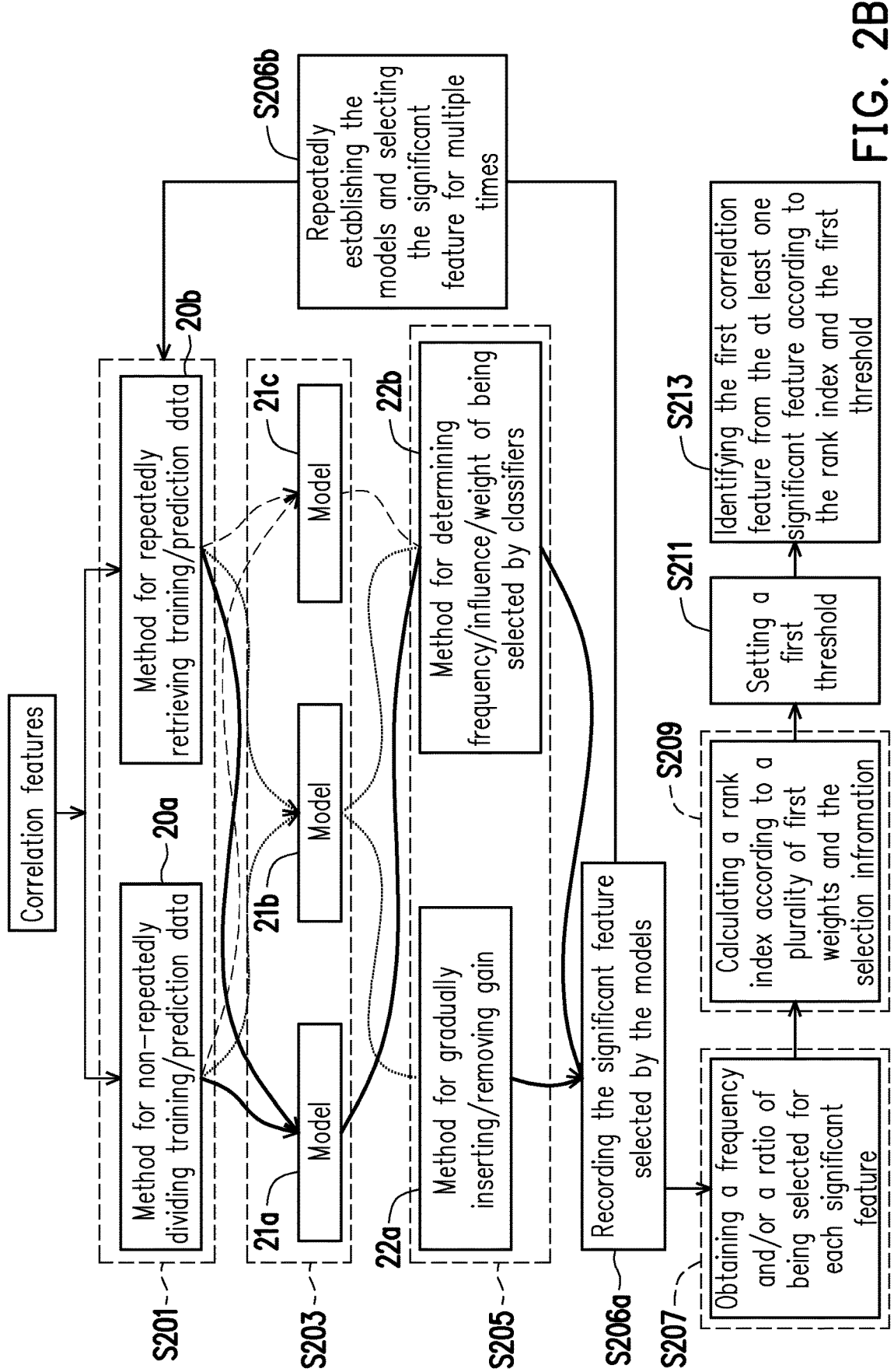

FIG. 2A and FIG. 2B are detailed flowcharts illustrating step S107 according to an embodiment of the invention.

Referring to FIG. 2A and FIG. 2B together, in step S201, the processor divides the plurality of correlation features into first training data and first prediction data. For example, as shown in FIG. 2B, in step S201, the processor may use a method for non-repeatedly dividing training/prediction data 20a and/or a method for repeatedly retrieving training/prediction data 20b to divide the first training data and the first prediction data. The method for non-repeatedly dividing training/prediction data 20a is, for example, K-fold CV algorithm, and the method for repeatedly retrieving training/prediction data 20b is, for example, Bootstrap algorithm. However, the invention is not limited in this regard.

In step S203, the processor establishes the plurality of first risk prediction models corresponding to a plurality of algorithms respectively according to the first training data. As shown in FIG. 2B, in step S203, the first training data is used to establish models 21a to 21c, for example. The model 21a is, for example, a model that combines with a plurality of classifier methods (e.g., Random Survival Forest). The model 21b is, for example, a model that uses a traditional statistical method (e.g., Cox proportional hazard). The model 21c is, for example, a model that uses the other method (e.g., Survival SVM).

Then, in step S205, the processor identifies at least one significant feature from the plurality of correlation features according to the plurality of first risk prediction models. It should be noted that, the significant feature may allow the models 21a to 21c to have a higher predictive accuracy. As shown in FIG. 2B, in step S205, for example, the significant feature is identified from the plurality of correlation features by using a method for gradually inserting/removing gain 22a (e.g., Stepwise (P-value/AIC) method) or using a method for determining frequency/influence/weight of being selected by classifiers 22b (e.g., an importance of the feature or a frequency of being selected). How to identify the features by using the method for gradually inserting/removing gain 22a or using a method for determining frequency/influence/weight of being selected by classifiers 22b may be learnt from the conventional art, which is not repeated herein.

After the significant feature is identified, in step S206a, the processor records the significant features selected by the models 21a to 21c. In addition, as shown by step S206b in FIG. 2B, step S201 to step S206a are repeatedly performed to repeatedly establish the models and select the significant feature for multiple times. This repeating process may be, for example, executed for a certain preset number of times.

Then, in step S207, the processor obtains selection information of being selected by each of the plurality of first risk prediction models for each of the at least one significant feature. Here, the selection information is, for example, a frequency and/or a ratio of being selected. With reference to Table 2:

TABLE 2

| Blood pressure feature | First result of model 21a | Second result of model 21a | First result of model 21b | Second result of model 21b | First result of model 21c | Second result of model 21c |
|---|---|---|---|---|---|---|
| F1 | 1 | 1 | 1 | 1 | 1 | 1 |
| F2 | 1 | 0 | 1 | 0 | 0 | 0 |
| F3 | 0 | 0 | 1 | 1 | 0 | 0 |

TABLE 2-continued

| Blood pressure feature | First result of model 21a | Second result of model 21a | First result of model 21b | Second result of model 21b | First result of model 21c | Second result of model 21c |
|---|---|---|---|---|---|---|
| F4 | 0 | 0 | 0 | 0 | 0 | 1 |
| F5 | 1 | 0 | 0 | 0 | 0 | 1 |

As shown in Table 2, it is assumed that there are currently blood pressure features F1 to F5. It is assumed that step S201 to step S206 are performed twice by the models 21a to 21c and the significant features selected by the models 21a to 21c are as shown in Table 2. In Table 2, the blood pressure features selected are indicated by "1", and the blood pressure features not selected are indicated by "0".

Then, the processor calculates the frequency and the ratio of being selected by each model for each of the features F1 to F5 according to the blood pressure features selected by each model, as shown in Table 3:

TABLE 3

| Blood pressure feature | Frequency (selected by model 21a) | Frequency (selected by model 21b) | Frequency (selected by model 21c) | Ratio (selected by model 21a) | Ratio (selected by model 21a) | Ratio (selected by model 21b) | Rank index |
|---|---|---|---|---|---|---|---|
| F1 | 2 | 2 | 2 | 1.0 | 1.0 | 1.0 | 1 |
| F2 | 1 | 1 | 0 | 0.5 | 0.5 | 0.0 | 1/3 |
| F3 | 0 | 2 | 0 | 0.0 | 1.0 | 0.0 | 1/3 |
| F4 | 0 | 0 | 1 | 0.0 | 0.0 | 0.5 | 1/6 |
| F5 | 1 | 0 | 1 | 0.5 | 0.0 | 0.5 | 1/3 |

Taking the feature F1 as an example, since the model 21a selects the blood pressure feature F1 in steps S201 to S206a which are repeated twice, the frequency at which the blood pressure feature F1 is selected by the model 21a may be recorded as "2" in Table 3. Also, since the blood pressure feature F1 is selected by the model 21a in both selections, the ratio at which the blood pressure feature F1 is selected by the model 21a may be recorded as "1" (i.e., 2/2). The frequency and the ratio of being selected by the models 21a to 21c for the other blood pressure features may be obtained in a manner similar to the above, which is not repeated hereinafter.

In addition, in step S209, the processor calculates at least one rank index respectively corresponding to the at least one significant feature according to a plurality of first weights respectively corresponding to the plurality of first risk prediction models and the selected information. It is assumed that one weight (i.e., the first weight described above) may be set for each model, and a score of each significant feature (i.e., the rank index) may be calculated according to the set weight and the selection information. For instance, if all the weights of the models 21a to 21c are ⅓, the processor may use, for example, the weight and the ratio of being selected by each model to calculate the rank index of the blood pressure feature F1 with a value of 1 (i.e., 1*⅓+1*⅓+1*⅓). The rank indexes of the other blood pressure features may be obtained in a manner similar to the above, which is not repeated hereinafter. In particular, the invention is not intended to limit the values of the weights corresponding to the models 21a to 21c. In an embodiment, the weight of the model 21a may 0, the weight of the model 21b may 0 and the weight of the model 21c may 1.

Then, in step S211, the processor sets a first threshold. In step S213, the processor identifies the first correlation feature from the at least one significant feature according to the at least one rank index and the first threshold. More specifically, if the first threshold is ⅕, the processor may select the blood pressure features F1, F2, F3 and F5 with the rank indexes greater than ⅕ as the first correlation feature. In particular, the invention is not intended to limit a value of the first threshold.

Referring back to FIG. 1, after step S107 is performed, in step S109, the processor establishes a plurality of second risk prediction models according to the at least one first correlation feature, and identifies, according to the plurality of second risk prediction models, at least one second correlation feature capable of predicting a specific disease from the at least one first correlation feature. Lastly, in step S111, the processor may output the second correlation feature as input in subsequent applications (e.g., trainings for other models or other applications). In particular, a detailed process of step S109 may be described by using FIG. 3A and FIG. 3B.

Figure 3A:
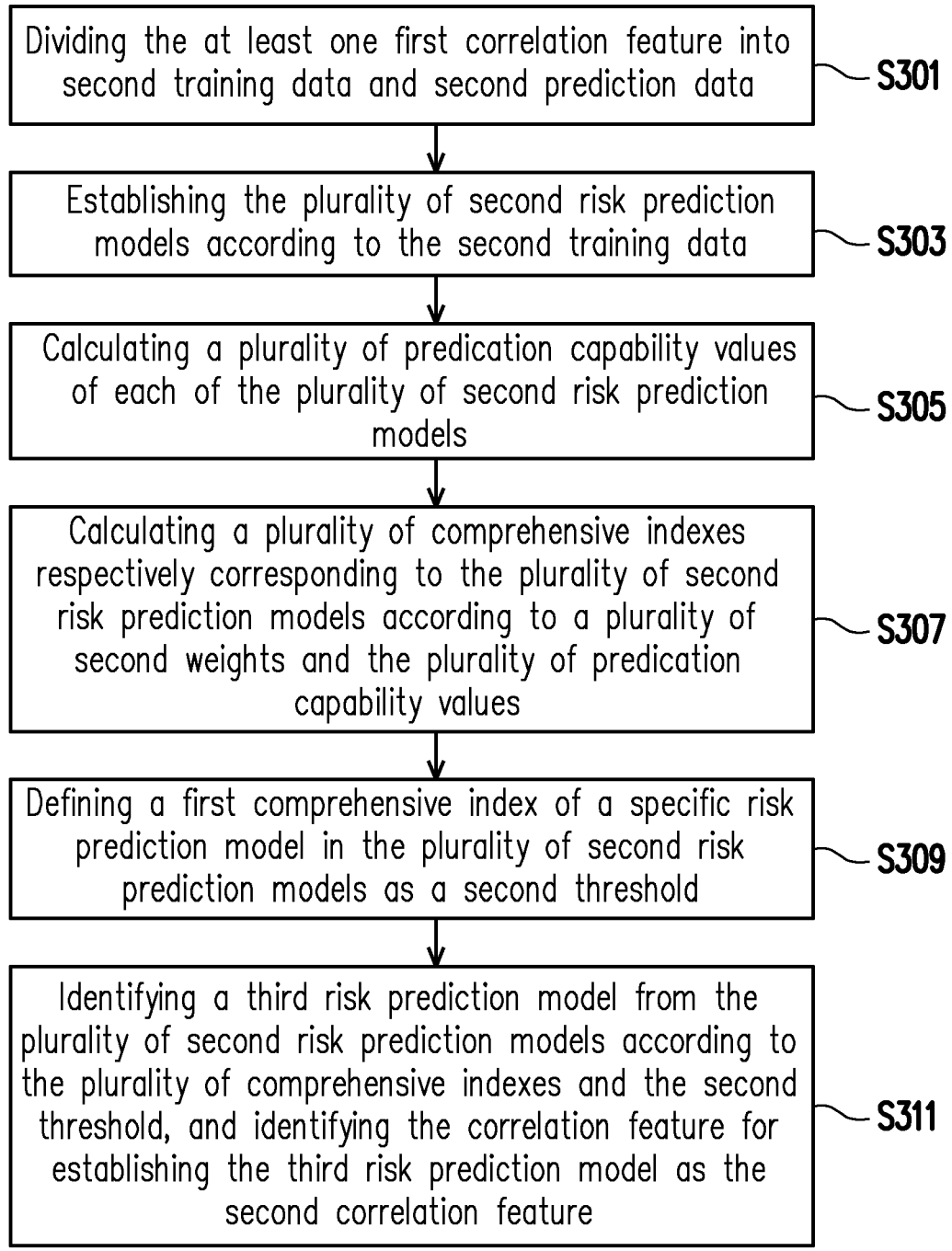
FIG. 3A and FIG. 3B are detailed flowcharts illustrating step S109 according to an embodiment of the invention.
Figure 3B:
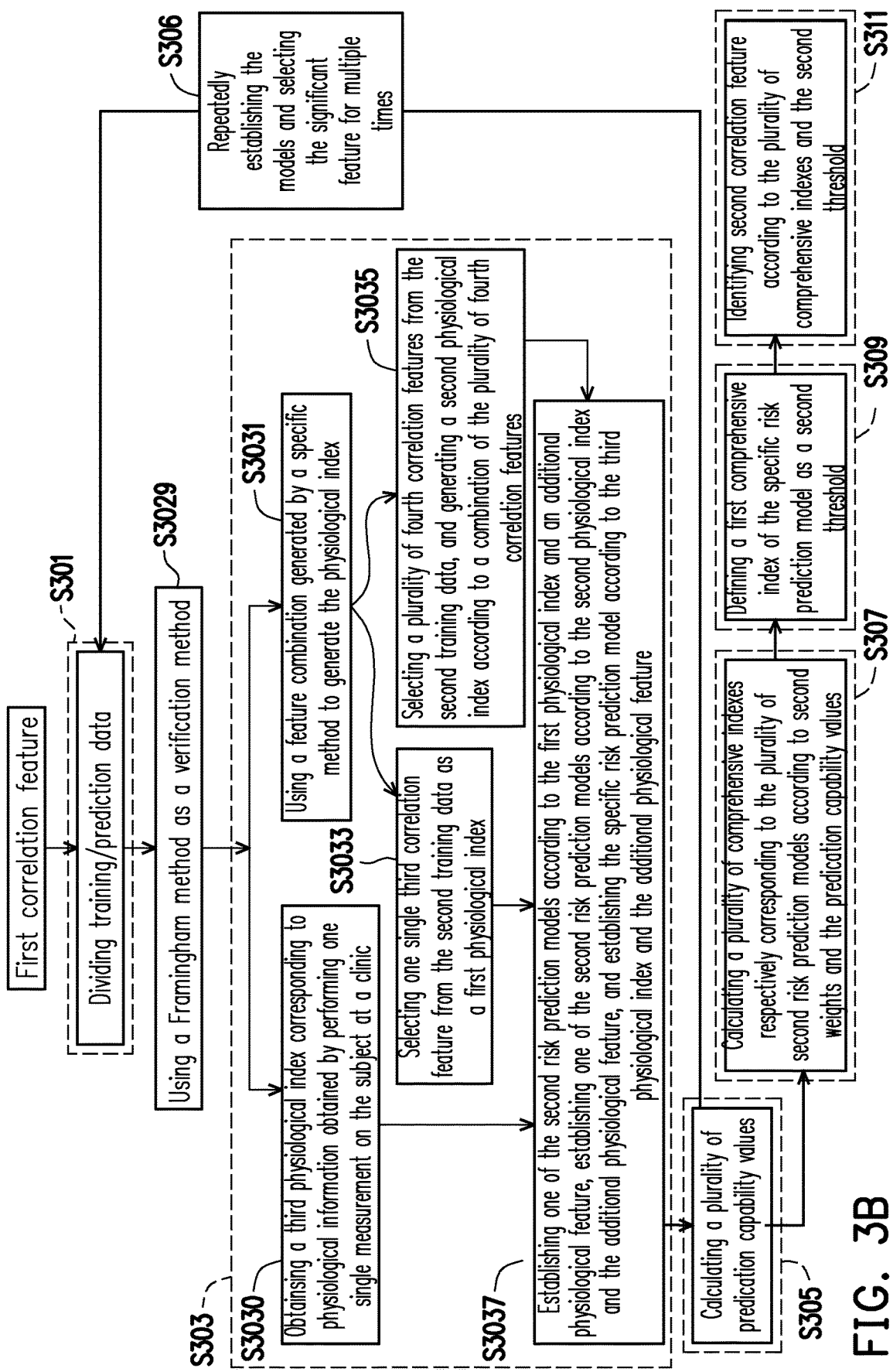

FIG. 3A and FIG. 3B are detailed flowcharts illustrating step S109 according to an embodiment of the invention.

Referring to FIG. 3A and FIG. 3B together, in step S301, the processor divides the at least one first correlation feature into second training data and second prediction data. A method for dividing the correlation feature into the training data and the prediction data may be similar to the method used in step S201, which is not repeated hereinafter. Then, in step S303, the processor establishes the plurality of second risk prediction models according to the second training data.

More specifically, referring to FIG. 3B, in step S303, a Framingham cardiovascular disease risk prediction method (hereafter, referred to as a Framingham method in short) is used to establish a risk prediction model. In general, the Framingham method is used to establish the risk prediction model by using the physiological index (e.g., systolic pressure) of the subject measured at a clinic and an additional physiological feature (e.g., age, total/high-density cholesterol, smoking and/or diabetes). Step S303 mainly establishes a plurality of models, and these models may include the specific risk prediction model established by using the traditional Framingham method. In addition, the models may extract at least one correlation feature from the second training material, use the correlation feature to generate a physiological index for the Framingham method and use the physiological index and the additional physiological feature to establish the risk prediction model. Finally, according to a prediction capability of the specific risk prediction model described above, the risk prediction model having a prediction capability greater than the prediction capability of the specific risk prediction model may be selected from the other risk prediction models established in step S303.

For example, step S303 may also include steps S3029 to step S3037. In step S3029, the processor uses the Framingham method as a verification method. In step S3030, the processor obtains a third physiological index corresponding to physiological information obtained by performing one single measurement on the subject at the clinic. In other words, the third physiological index obtained in step S3030 is used for establishing a traditional risk prediction model (e.g., the specific risk prediction model described above). Further, in step S3031, a feature combination generated by a specific method is used to generate a physiological index for establishing the risk prediction model. Step S303 may further be divided into steps S3033 and step S3035. In step S3033, the processor selects one single correlation feature (a.k.a. a third correlation feature) from the second training data as a first physiological index for establishing the risk prediction model. The third correlation feature may be a log of the average systolic pressure in one day or other correlation features, which are not particularly limited herein. In step S3035, the processor selects a plurality of correlation features (a.k.a. fourth correlation features) from the second training data, and generates a second physiological index according to a combination of the plurality of fourth correlation features. The detailed execution process of step S3035 is described in detail later.

Then, in step S307, the processor establishes one of the second risk prediction models according to the first physiological index and the additional physiological feature, establishes one of the second risk prediction models according to the second physiological index and the additional physiological feature, and establishes the specific risk prediction model according to the third physiological index and the additional physiological feature In other words, the processor establishes the second risk prediction models by using the physiological indexes respectively generated in step S3030, step S3033 and step S3035 together with the additional physiological feature.

After the plurality of second risk prediction models are established, in step S305, the processor calculates a plurality of predication capability values of each of the plurality of second risk prediction models. More specifically, the predication capability values of the risk prediction model may be calculated by methods for predication capability values C-index, AIC or BIC. Taking C-index as an example, C-index is used to measure a consistency between the risk prediction model and an actual observation result with a value ranges from 0 to 1. For example, if the risk prediction model predicts that cardiovascular risk values of the three subjects are 1, 2, and 3, respectively (where the higher value indicates a higher change of getting cardiovascular disease) and time lengths of the subjects actually getting cardiovascular disease during observation period are 5 years, 3 years and 1 year, respectively. For the first and second subjects, the second subject has the higher risk value, which is consistent with the fact that the second subject gets cardiovascular disease faster. Therefore, as a comparison result of the three subjects, there are a total of three combinations in a pairwise comparison. In this example, since there are three combinations that conform to the consistency, C-index may be recorded as "1". Based on this method, the predication capability values of each second risk prediction model may be obtained. In addition, as shown by step S306 in FIG. 3B, the processor repeatedly establishes the models and selects the significant feature for multiple times. That is to say, steps S303 to S305 may be repeated for a plurality of times (i.e., a plurality of rounds), and the prediction capability value of each model may be obtained each time. With reference to Table 4:

TABLE 4

| Repeat order | C-index of risk prediction model established by using physiological index of step S3030 | C-index of risk prediction model established by using physiological index of step S3033 | C-index of risk prediction model established by using physiological index of step S3035 |
| --- | --- | --- | --- |
| 1st time | 0.70 | 0.65 | 0.75 |
| 2nd time | 0.75 | 0.70 | 0.80 |

In the example of Table 4, it is assumed that, "risk prediction model established by using the physiological index of step S3030" is a model established by using the physiological index corresponding to the physiological information obtained by performing one single measurement on the subject at the clinic, "risk prediction model established by using physiological index of step S3033" is a model established by using the physiological index generated by using only the blood pressure feature F1, and "risk prediction model established by using physiological index of step S3035" is a model established by using the physiological indexes generated by using the blood pressure features F1, F2, F3 and F5 with the top four rank indexes. After aforesaid three models are established with reference to the Framingham method, the processor may, for example, repeatedly perform steps S303 and S305 for two rounds to obtain C-index calculated by each model in each round. As shown in Table 5, for "C-index of risk prediction model established by using physiological index of step S3030", C-index with a value of "0.70" is obtained after the first round and C-index with a value of "0.75" is obtained after the second round. C-indexes obtained by the other models in each round are as shown in Table 4, and will not be described hereinafter.

Then, in step S307, the processor calculates a plurality of comprehensive indexes respectively corresponding to the plurality of second risk prediction models according to a plurality of second weights and the plurality of predication capability values. For example, as continued from Table 4, in Table 5:

TABLE 5

| | Risk prediction model established by using physiological index of step S3030 | Risk prediction model established by using physiological index of step S3033 | Risk prediction model established by using physiological index of step S3035 |
|---|---|---|---|
| Comprehensive index | 0.725 | 0.675 | 0.775 |

For example, the processor may set a weight of C-index obtained each time as 0.5, and then calculate the comprehensive indexes of the three models. Taking "C-index of risk prediction model established by using physiological index of step S3030" as an example, a value of the comprehensive index is 0.725 (i.e., (0.70*0.5)+(0.75*0.5)). The comprehensive indexes of the other models in Table 5 may be calculated in a manner similar to the above, which is not repeated hereinafter.

Then, in step S309, the processor defines a first comprehensive index of a specific risk prediction model in the plurality of second risk prediction models as a second threshold. In other words, the processor defines the comprehensive index of "the risk prediction model established by using physiological index of step S3030" as the second threshold. In particular, "the risk prediction model established by using physiological index of step S3030" is the traditional risk prediction model established by using the physiological index obtained by performing one single measurement on the subject at the clinic. When the comprehensive index of one risk prediction model is greater than the second threshold, the prediction capability of that risk prediction model is better than the risk prediction model established by using the traditional method.

After the second threshold is defined, in step S311, the processor identifies a third risk prediction model from the plurality of second risk prediction models according to the plurality of comprehensive indexes and the second threshold, and identifies the correlation feature for establishing the third risk prediction model as the second correlation feature. Specifically, in the example of Table 5, the processor selects the value of the comprehensive index of "the risk prediction model established by using physiological index of step S3030" (i.e., 0.725) as the second threshold, identifies "the risk prediction model established by using physiological index of step S3035" having the comprehensive index greater than the second threshold from the remaining two models as the third risk prediction model, and identifies the correlation feature for establishing the third risk prediction model as the second correlation feature.

In particular, although the prediction capability value of the invention is described by taking C-index as an example, the invention is not limited thereto. In other embodiments, C-index may be replaced by AIC or BIC. In this case, in step S311, the model having the comprehensive index less than the second threshold is selected as the third risk prediction model.

Figure 4:
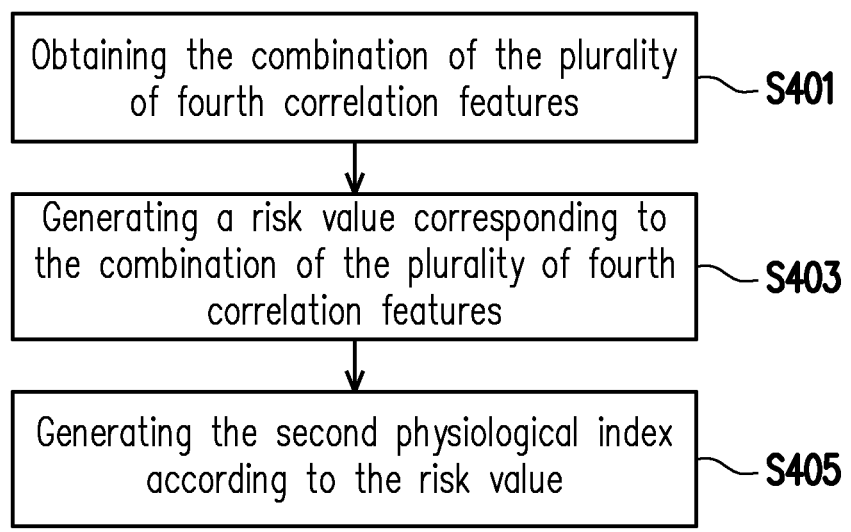
FIG. 4 is a detailed flowchart illustrating step S3035 according to an embodiment of the invention.

Further, FIG. 4 is a detailed flowchart illustrating step S3035 according to an embodiment of the invention.

Referring to FIG. 4, in step S401, the processor obtains the combination of the plurality of fourth correlation features. For example, in an embodiment, the processor selects the plurality of fourth correlation features from the second training data. The selection information (i.e., the frequency and/or the ratio) of being selected by each of the first risk prediction models for the fourth correlation features is greater, compared to the other correlation features in the second training data. For instance, the frequency and/or the ratio of each blood pressure feature selected by each model may be calculated by the method of Table 3 so as so that the rank index of each blood pressure feature may then be obtained. Then, four blood pressure features with the greatest rank indexes are selected as the fourth correlation features, and these four correlation features are then used as the combination of the fourth correlation feature.

In addition, in an embodiment, after the processor selects the fourth correlation features from the second training data by the method described above, the processor may also generate at least one feature interaction term according to these fourth correlation features, and use the selected fourth correlation features and the generated feature interaction term together as the combination of the fourth correlation features. In particular, the feature interaction term may be a product of any two correlation features among the fourth correlation features. Taking the blood pressure features F1 to F5 as an example, assuming that the processor selects the blood pressure features F1, F2, F3 and F5 as the fourth correlation features, the processor then multiplies any two blood pressure features among the blood pressure features F1, F2, F3 and F5 to generate six feature interaction terms in total, and finally use the blood pressure features F1, F2, F3 and F5 and the generated six feature interaction terms as the combination of the fourth correlation features.

Alternatively, in another embodiment, the processor obtains a plurality of classes by classifying the correlation features in the second training data according to a type (e.g., systolic pressure, diastolic pressure, heart rate) of the physiological information (e.g., the blood pressure) and a calculation method of the correlation features in the second training data (e.g., average and highest/lowest, standard deviation and range of change, sudden rising slope and difference in different time intervals), then identifies the correlation features having a greatest rank index in each of the classes as the plurality of fourth correlation features, and uses the four fourth correlation features as the combination of the fourth correlation features. For instance, as shown in Table 6:

TABLE 6

| Blood pressure feature | Actual feature name | Feature rank index | Blood pressure Type | Calculation method | Type tag | Sort by |
|---|---|---|---|---|---|---|
| F1 | Log of average systolic pressure | 1 | Systolic pressure | Average and highest/lowest | 1 | 1 |
| F2 | Square of sudden rising slop of diastolic pressures from sleep until wake-up | 1/3 | Diastolic pressure | Sudden rising slope and difference in different time intervals | 2 | 1 |
| F3 | Square root of diastolic pressures in one day | 1/3 | Diastolic pressure | Standard deviation and range of change | 3 | 1 |
| F5 | Lowest diastolic pressure during sleep | 1/3 | Systolic pressure | Average and highest/lowest | 1 | 2 |

As shown in Table 6, if a blood pressure type of one blood pressure feature and a calculation method of that blood pressure feature are the same as a blood pressure type of another blood pressure feature and a calculation method of said another blood pressure feature, these two blood pressure features may be classified as the same class. For example, because the blood pressure types of the blood pressure feature F1 and the blood pressure feature F5 are both "Systolic pressure" and the calculation methods of the blood pressure feature F1 and the blood pressure feature F5 are both "Average and highest/lowest", the blood pressure feature F1 and the blood pressure feature F5 are both classified as the same class. In Table 6, the type tag "1" is used to indicate that the blood pressure feature F1 and the blood pressure feature F5 belong to the same class. In addition, since the blood pressure type and the calculation method of the remaining blood pressure feature F2 and the blood pressure feature F3 are not exactly the same and the blood pressure type and the calculation method of the blood pressure feature F2 and the blood pressure feature F3 are not exactly the same as the blood pressure feature F1 and the blood pressure feature F5, the processor separately classifies the blood pressure feature F2 into one class (marked with the type tag "2") and separately classifies the blood pressure feature F5 into one category (marked with the type tag "3"). Then, the processor selects the correlation feature having the greatest rank index from each class. In this example, the processor selects the blood pressure feature F1 from the class with the type tag "1", selects the blood pressure feature F2 from the class with the type tag "2", selects the blood pressure feature F3 from the class with the type tag "3", identifies the blood pressure features F1 to F3 as the fourth correlation features, and uses these three fourth correlation features as the combination of the fourth correlation features.

Alternatively, in another embodiment, the processor may also select the fourth correlation features from the second training data by using a principal components analysis (PCA), and generate the combination of the fourth correlation features according to the fourth correlation features. How to use the principal component analysis for selection can be known from the conventional art, which is not repeated herein.

Then, in step S403, the processor generates a risk value corresponding to the combination of the plurality of fourth correlation features. For example, the processor may utilize Coxph algorithm to calculate the risk value of the combination of the of fourth correlation features. The risk value is, for example, a risk, a probability and/or a time of disease.

After the risk value is obtained, in step S405, the processor generates the second physiological index according to the risk value. For example, in an embodiment, the processor directly uses the risk value as the second physiological index. Alternatively, in another embodiment, the processor may also use the normalized risk value as the second physiological index.

In summary, in the feature identifying method and the electronic device of the invention, according to the physiological information obtained by measuring the subject at the different time points in one day (24 hours), the features capable of predicting the specific disease may be found from the physiological information. These features may be used to assist doctors in determining the risk of the specific disease, or used in subsequent model training or medical research. In particular, the invention utilizes long-term physiological information for analysis and obtains the features capable of predicting the specific disease according to the statistics and machine learning methods with a considerable number of correlation features taken into consideration. The features have better predictive results than those of the traditional method (e.g., the Framingham method) to improve the predictive accuracy for the risk of disease and help reducing the likelihood of medical misjudgment. In the example of blood pressure, for patients who may have cardiovascular disease in the future, in addition to monitoring abnormalities regarding whether systolic pressure and diastolic pressure are too high or too low, the features may also be used as important factors for double checking the abnormalities, so as to improve a correct credibility of determination, thereby avoiding delays in accepting the relevant treatment.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A feature identifying method for an electronic device, the method comprising:
   obtaining a plurality of physiological information obtained by measuring a subject at a plurality of time points in one day, wherein the physiological information comprises blood pressure information;
   converting the plurality of physiological information into a plurality of correlation features corresponding to the plurality of physiological information respectively;
   establishing a plurality of first risk prediction models corresponding to a plurality of algorithms according to the plurality of correlation features, and identifying at least one significant feature from the plurality of correlation features according to the plurality of first risk prediction models and identifying at least one first correlation feature from the at least one significant feature according to selection information of being selected by each of the plurality of first risk prediction models for each of the at least one significant feature, wherein the step of establishing the first risk prediction models according to the plurality of correlation features comprises training one of the first risk prediction models according to a machine learning method;

establishing a plurality of second risk prediction models by using a Framingham cardiovascular disease risk prediction method according to the at least one first correlation feature, and identifying at least one second correlation feature capable of predicting a cardiovascular disease from the at least one first correlation feature according to a plurality of predication capability values of the plurality of second risk prediction models;

outputting the at least one second correlation feature; and predicting a risk of the cardiovascular disease by using the at least one second correlation feature found from the physiological information measured at the time points in one day.

2. The feature identifying method according to claim 1, wherein the step of converting the plurality of physiological information into the plurality of correlation features corresponding to the plurality of physiological information respectively comprises:

performing a feature engineering for converting the plurality of physiological information into a plurality of converted features respectively; and converting the plurality of converted features into the plurality of correlation features respectively according to at least one of a linear transformation algorithm and a non-linear transformation algorithm.

3. The feature identifying method according to claim 1, wherein the step of establishing the plurality of first risk prediction models corresponding to the algorithms according to the plurality of correlation features comprises:

dividing the plurality of correlation features into first training data and first prediction data; and establishing the plurality of first risk prediction models corresponding to the algorithms respectively according to the first training data.

4. The feature identifying method according to claim 3, wherein the step of identifying the at least one first correlation feature from the at least one significant feature according to the selection information of the at least one significant feature comprises:

obtaining the selection information of being selected by each of the plurality of first risk prediction models for each of the at least one significant feature;

calculating at least one rank index respectively corresponding to the at least one significant feature according to a plurality of first weights respectively corresponding to the plurality of first risk prediction models and the selected information; and identifying the first correlation feature from the at least one significant feature according to the at least one rank index and a first threshold.

5. The feature identifying method according to claim 1, wherein the step of establishing the plurality of second risk prediction models by using the Framingham cardiovascular disease risk prediction method according to the at least one first correlation feature, and identifying, according to the plurality of predication capability values of the plurality of second risk prediction models, the at least one second correlation feature capable of predicting the specific disease from the at least one first correlation feature comprises:

dividing the at least one first correlation feature into second training data and second prediction data;

establishing the plurality of second risk prediction models according to the second training data;

calculating the plurality of predication capability values of each of the plurality of second risk prediction models;

calculating a plurality of comprehensive indexes respectively corresponding to the plurality of second risk prediction models according to a plurality of second weights and the plurality of predication capability values; and defining a first comprehensive index of a specific risk prediction model in the plurality of second risk prediction models as a second threshold, identifying a third risk prediction model from the plurality of second risk prediction models according to the plurality of comprehensive indexes and the second threshold, and identifying the correlation feature for establishing the third risk prediction model as the second correlation feature.

6. The feature identifying method according to claim 5, wherein the step of establishing the plurality of second risk prediction models according to the second training data comprises:

selecting one single third correlation feature from the second training data as a first physiological index, and establishing one of the plurality of second risk prediction models according to the first physiological index and an additional physiological feature;

selecting a plurality of fourth correlation features from the second training data, generating a second physiological index according to a combination of the plurality of fourth correlation features, and establishing one of the plurality of second risk prediction models according to the second physiological index and the additional physiological feature; and establishing the specific risk prediction model according to a third physiological index corresponding to physiological information obtained by performing one single measurement on the subject once and the additional physiological feature.

7. The feature identifying method according to claim 6, wherein the step of selecting the plurality of fourth correlation features from the second training data, and generating the second physiological index according to the combination of the plurality of fourth correlation features comprises:

selecting the plurality of fourth correlation features from the second training data, wherein the selection information of being selected by each of the plurality of first risk prediction models for the plurality of fourth correlation features is greater, compared to the other correlation features in the second training data.

8. The feature identifying method according to claim 6, wherein the step of selecting the plurality of fourth correlation features from the second training data, and generating the second physiological index according to the combination of the plurality of fourth correlation features comprises:

selecting the plurality of fourth correlation features from the second training data, generating at least one feature interaction term, and generating the combination of the plurality of features according to the plurality of fourth correlation features and the at least one feature interaction term.

9. The feature identifying method according to claim 6, wherein the step of selecting the plurality of fourth correlation features from the second training data, and generating the second physiological index according to the combination of the plurality of fourth correlation features comprises:
  obtaining a plurality of classes by classifying the correlation features in the second training data according to a type of the physiological information a calculation method of the correlation features in the second training data; and
  identifying the correlation feature having a greatest rank index in each of the plurality of classes as the plurality of fourth correlation features.

10. The feature identifying method according to claim 6, wherein the step of selecting the plurality of fourth correlation features from the second training data, and generating the second physiological index according to the combination of the plurality of fourth correlation features comprises:
  selecting the plurality of fourth correlation features from the second training data by using a principal components analysis (PCA).

11. The feature identifying method according to claim 6, wherein the step of generating the second physiological index according to the combination of the plurality of fourth correlation features comprises:
  generating a risk value corresponding to the combination of the plurality of fourth correlation features; and
  generating the second physiological index according to the risk value.

12. An electronic device, comprising:
  a memory circuit, configured to store at least one instruction; and
  a processor, configured to execute the at least one instruction to:
  obtain a plurality of physiological information obtained by measuring a subject at a plurality of time points in one day, wherein the physiological information comprises blood pressure information;
  convert the plurality of physiological information into a plurality of correlation features corresponding to the plurality of physiological information respectively;
  establish a plurality of first risk prediction models corresponding to a plurality of algorithms according to the plurality of correlation features, and identify at least one significant feature from the plurality of correlation features according to the plurality of first risk prediction models and identifies at least one first correlation feature from the at least one significant feature according to selection information of being selected by each of the plurality of first risk prediction models for each of the at least one significant feature, wherein the processor is configured to train one of the first risk prediction models according to a machine learning method;
  establish a plurality of second risk prediction models by using a Framingham cardiovascular disease risk prediction method according to the at least one first correlation feature, and identify at least one second correlation feature capable of predicting a cardiovascular disease from the at least one first correlation feature according to plurality of predication capability values of the plurality of second risk prediction models; and
  output the at least one second correlation feature, and predict a risk of the cardiovascular disease by using the at least one second correlation feature found from the physiological information measured at the time points in one day.

* * * * *